(12) United States Patent
Takami

(10) Patent No.: US 7,102,750 B2
(45) Date of Patent: Sep. 5, 2006

(54) METHOD OF IN-SITU MONITORING OF CRYSTALLIZATION STATE

(75) Inventor: Yoshio Takami, Isehara (JP)

(73) Assignee: Kabushiki Kaisha Ekisho Sentan Gijutsu Kaihatsu Center, Yokohama (JP)

(*) Notice: Subject to any disclaimer, the term of this patent is extended or adjusted under 35 U.S.C. 154(b) by 302 days.

(21) Appl. No.: 10/651,900

(22) Filed: Aug. 29, 2003

(65) Prior Publication Data

US 2005/0078298 A1   Apr. 14, 2005

(30) Foreign Application Priority Data

Aug. 29, 2002 (JP) ............................. 2002-251853
Jun. 27, 2003 (JP) ............................. 2003-184415

(51) Int. Cl.
  *G01N 21/00* (2006.01)
(52) U.S. Cl. ...................................... 356/432; 356/445
(58) Field of Classification Search ............. 356/237.1, 356/30, 432, 445, 237.2, 237.6
  See application file for complete search history.

(56) References Cited

U.S. PATENT DOCUMENTS 6,633,831 B1 * 10/2003 Nikoonahad et al. ....... 702/155

FOREIGN PATENT DOCUMENTS

JP   09-314065   6/1999
JP   2000-396474   9/2001

OTHER PUBLICATIONS

Article entitled, "Excimer Laser-Induced Temperature Field in Melting and Resolidification of Silicon Thin Films", published in *Journal of Applied Physics*, vol. 87, No. 1, dated Jan. 1, 2000.

* cited by examiner

*Primary Examiner*—Hoa Q. Pham
*Assistant Examiner*—Roy M. Punnoose
(74) *Attorney, Agent, or Firm*—Graybeal Jackson Haley LLP

(57) ABSTRACT

A method of in-situ monitoring of a crystallization state is used for laser anneal processing for applying an energy line irradiation for at least one of crystallization of a thin film and promotion of the crystallization. The method of in-situ monitoring of a crystallization state is characterized by irradiating simultaneously at least a plurality of monitoring places in a region having a predetermined area of at least one of the surface and the underside of the thin film by a monitor light for monitoring a crystallization state of the thin film at least during or after of before, during and after the energy line irradiation directly or through a substrate, and measuring a temporal change of the intensity of at least one of a reflected light and a transmitted light, from the surface or the underside of the thin film, of the monitor light as a light intensity distribution related to the positions of the monitoring places.

15 Claims, 8 Drawing Sheets

METHOD OF IN-SITU MONITORING OF CRYSTALLIZATION STATE

CROSS-REFERENCE TO RELATED APPLICATION

Priority is claimed to Japanese patent application No. 2002-251853, filed Mar. 29, 2002, and Japanese patent application No. 2003-184415, which are incorporated by reference.

BACKGROUND OF THE INVENTION

1. Field of the Invention

The present invention relates to a method and apparatus for in-situ monitoring of a crystallization state to be carried out to monitor the crystallization state of a thin film in a process of anneal processing using an energy line (e.g., laser beam) as well as an annealing method and device using the method of in-situ monitoring of a crystallization state. The method and apparatus for in-situ monitoring of a crystallization state are used, for example, for monitoring the crystallization state when annealing (e.g., laser annealing process) an amorphous semiconductor thin film in a process for producing a thin film transistor for a switching element or device of a liquid crystal display or an organic electroluminescence (hereinafter to be called "EL") display.

2. Description of the Prior Art

Conventionally, there has been a method of detecting the intensity of a reflected light from one locally irradiated place which is irradiated by an annealing area with a monitor light, as a method of monitoring crystallization of an amorphous silicon thin film formed on a glass substrate, for example, when crystallizing the film by laser annealing (See, e.g., Patent Document 1, Patent Document 2 and non-patent document 1).

Patent Document 1: JP Patent Appln. Public Disclosure No. 2001-257176.

Patent Document 2: JP Patent Appln. Public Disclosure No. 11-148883.

Non-Patent Document 1: "Excimer Laser-Induced Temperature Field in Melting and Resolidification of Silicon Thin Films" by M. Hatano, S. Moon, M. Lee, K. Suzuki and C. P. Grigoropoulos, in Journal of Applied Physics, Vol. 87, pp. 36–43, published in 2000.

According to the foregoing non-patent document 1, a continuous wave laser beam (hereinafter to be called "CW laser"), that is, a helium neon (He—Ne) laser beam having a wavelength of about 633 nm, concretely, is used as a monitor light, the laser beam is applied to the thin film, a reflected light from the thin film is detected by a silicon PN junction photo diode type photo detector having a response time of 1 nanosecond (hereinafter to be called "ns"), and a temporal change of a detected signal waveform is measured by a sampling oscilloscope which samples a frequency signal of 1 GHz.

In this document, a pulsed laser beam, that is, concretely, a krypton fluorine (KrF) excimer laser beam in an ultraviolet area having a pulse width of about 25 ns (a value in full width at half maximum, hereinafter to be called "FWHM") and a wavelength of about 248 nm is used as an annealing laser beam for melting the thin film. Also, a laser fluence is made around 500 mJ/cm$^2$.

Besides the above document, there is a method of crystallization wherein, as an annealing laser beam for melting a thin film, a reshaped laser beam in which a xenon chlorine (XeCl) excimer laser having energy of about 1 J per pulse is reshaped to a strip-like elongate beam (350 mm×1 mm=3.5 cm$^2$), and the reshaped laser beam is linearly scanned to irradiate a large-area substrate at a fluence of about 300 mJ/cm$^2$.

A dehydrogenated amorphous silicon thin film having a film thickness of several decades nm is melted by irradiation with an annealing laser beam for several decades to 100 ns, which causes crystallization. The silicon increases its light reflectivity, taking on a metallic nature when melted, and the light reflection intensity of the silicon thin film increases. The method of investigating crystallization as shown in the foregoing document detects by the photo detector a temporal change of the light reflection intensity accompanying the melting of the thin film.

According to the conventional method of investigating crystallization, a location (substantially one position) of an area for melting by annealing laser beam is irradiated by a monitor light, and only the reflected light from the location is detected.

The crystallization of the thin film, namely, the speed and direction of growth of the crystal grain as well as the grain diameter are not uniform actually within an area irradiated by an annealing laser beam. The energy of the annealing laser beam, influenced by the shape of a patterned film, difference in deviation of the film thickness of an amorphous silicon (hereinafter to be called "a-Si") thin film as a precursor, etc., is not transmitted inside the thin film as previously intended. As a result, the crystal grains are not grown as anticipated, and there used to be caused a dispersion in crystallization of the thin film within the area irradiated by the annealing laser beam.

There is a case where, in order to promote crystal growth of a thin film in the direction of the substrate surface, that is, the lateral direction, a laser energy distribution within the area to be irradiated by the annealing laser beam is intentionally made uneven, or the irradiation pattern of the laser is made asymmetrical. In this case, also, the energy of the annealing laser beam, influenced by the shape of the thin film pattern and others as mentioned above, is not transmitted inside the thin film as previously intended. As a result, the crystal grains were not grown inside the thin film as anticipated.

Due to the dispersion in crystallization of the thin film within the area irradiated by the annealing laser beam, there is caused a difference in investigation results of the crystallization of the thin film depending on which part of the area to be monitored by the monitor light. In other words, the melting area of the thin film is not uniform.

A thin film transistor which has undergone laser-anneal processing on the basis of such an erroneous measurement result of crystallization has a feature out of a predetermined range, and a failure, for example, in electrical feature was caused in a liquid crystal display/using this thin film transistor as a switching element or device.

In this way, the conventional art was intended for detecting the crystallization of a thin film by a photo diode on the basis of a piece of information, that is, the information obtained from a reflected light caused by irradiating substantially one-point place of an area for melting the thin film by an annealing energy line (e.g., laser beam).

An object of the present invention lies in accurately observing a crystallization state of a thin film with a monitor light with a high time resolution in real time, which enables to monitor, in an area to be irradiated by an energy line, positions varied from melting to solidification and crystallization.

SUMMARY OF THE INVENTION

The method of in-situ monitoring of crystallization state according to the present invention is a method of in-situ monitoring of a crystallization state in annealing processing by an energy line irradiation for at least one of crystallization of a thin film and promotion of the crystallization, comprising: a step of irradiating by a monitor light simultaneously at least a plurality of monitoring places in a region having a predetermined area of at least one of the surface and the underside of said thin film directly or through a substrate, at least during or after of before, during and after said energy line irradiation, said monitor light being for monitoring of the crystallization state of said thin film; and a step of measuring a temporal change of the intensity of at least one of a reflected light and a transmitted light, from said surface or said underside of said thin film, said monitor light as a light intensity distribution related to the positions of said monitoring places.

Another method of in-situ monitoring of crystallization state according to the present invention is a method of in-situ monitoring of a crystallization state in an annealing processing by an energy line irradiation for crystallization of a thin film or promotion of the crystallization, comprising: a step of irradiating by a monitor light simultaneously at least a plurality of monitoring places in a region having a predetermined area, of said thin film at least during or after of before, during and after said energy line irradiation, said monitor light being for monitoring of the crystallization state of said thin film; and a step of measuring a temporal change of the intensity of the reflected light or the transmitted light, from said thin film, said monitor light as a light intensity distribution related to the positions of said monitoring places, wherein said measuring step comprises: receiving at least one of the reflected light and the transmitted light from said thin film and generating an electron corresponding to the received light by photoelectric conversion; passing the generated electron through a field which changes with time; receiving the passed electron for forming a projected image corresponding to the passed electron in a display screen; and measuring the temporal change of the intensity distribution of said projected image.

At least each monitoring place is simultaneously irradiated by the monitor light, and the light intensity distribution with the temporal change of the intensity of the light related to each monitoring place is measured. Even if dispersion is caused in crystallization of the thin film within an area to be irradiated by the annealing energy line, the dispersion in crystallization of the thin film can be confirmed and the crystallization state of the thin film can be accurately observed by measuring the light intensity distribution which includes the temporal change and is related to the position of each monitoring place, on the basis of the light from each monitoring place.

According to the present invention, when an annealed thin film is, for example, an amorphous silicon thin film, both the time for melting and crystallizing from when the silicon is melted until it is solidified and crystallized and the speed (information at the position of the monitoring place) of crystal growth (e.g., lateral growth) can be measured. In other words, it is possible to know the position of a boundary face (solid-liquid boundary face) between a solid phase and a liquid phase when the silicon melts and crystallizes and the speed of movement. Since the crystallization state of the silicon thin film can be accurately observed, it is possible to obtain an optimum temperature gradient of the change from melting to solidification of the thin film and an optimum intensity distribution of the energy line (e.g., excimer laser beam) (to obtain an optimum condition), which facilitates production control in a production line.

Also, according to the present invention, the crystallization state of the silicon thin film can be accurately observed, so that the method and apparatus for in-situ monitoring of the crystallization state can be effectively utilized in developing a high-quality crystallized silicon thin film with few drawbacks as a thin film.

Also, according to the present invention, a light intensity distribution which includes a temporal change formed in a display screen and related to the position of each place for monitoring can be measured from the temporal change of the intensity distribution of a projected image. Furthermore, by determining a rate of the temporal change of the field in the measuring step in correspondence to the speed of the change from melting to solidification in crystallization of the thin film or promoting the crystallization, it is possible to observe very accurately the change of the film quality from before melting to melting as well as crystallization in the area in the region to be irradiated by the energy line.

According to the present invention, if the irradiation is performed with the energy line by using a phase shifter, it is possible to observe the crystallization state from the formation of a core as a starting point of the crystal growth generated by irradiating the thin film with the energy line passing the phase shifter and over a period of during, before and after a process of lateral crystal growth of the thin film, by the irradiation with the monitor light before and during the irradiation with the energy line using the phase shifter for the formation of the core of the crystal growth and before and during the irradiation with the energy line using the phase shifter for the lateral crystal growth. On the basis of the result of such monitoring, it is possible to obtain an appropriate condition for irradiation with the energy line for the lateral crystal growth of the thin film. Consequently, a large crystal grain can be formed. For example, in manufacturing a thin film transistor, an active layer or a channel area can be made up of one crystal grain. In other words, the channel area can be formed substantially from a single crystal.

The irradiation by said monitor light in said irradiation step by said monitor light can be applied to a slit-like irradiation region of said thin film so that said irradiation by said monitor light is applied simultaneously to said plurality of monitoring places. By this, the process of the lateral growth of the thin film can be efficiently and accurately observed.

The foregoing irradiation by the energy line can be made by a pulsed light.

In the measuring step, the reflected light or the transmitted light, from the thin film, of the monitor light can be detected by a streak camera. This enables to obtain the speed of the change of the film quality before melting of the thin film, from solidification to crystallization and information on position relative to a melting region and a non-melting region (i.e., the position of the solid-liquid boundary face) by a high time resolution, and the lateral growth of the thin film can be accurately observed.

It is also possible to have the monitor light reshaped and irradiated such that said monitor light may have a section of which the area includes the plurality of monitoring places on said thin film, and to reshape at least one of the reflected light and the transmitted light from the thin film into a strip-like form and make it incident on a light receiving portion of a photoelectric converter. In this way, the light from the place for monitoring is incident on the light receiving portion of the photoelectric converting portion in a strip form.

In place thereof, it is also possible to apply an irradiation by a plurality of said monitor lights simultaneously to said plurality of monitoring places, and to make at least one of the reflected light and the transmitted light from said surface or said underside of said thin film incident on the photoelectric converter so that said plurality of lights may align.

Furthermore, it is possible to irradiate said monitor light on said thin film by means of one object lens and image the reflected light from said thin film on said photoelectric converter, and to make at least one of said reflected light and said transmitted light via said object lens take separate optical paths. In this way, the image formation of both the incident light of the monitor light on the thin film and the light reflected from the thin film can be made by use of a single object lens The foregoing thin film may include at least one of a thin film mainly composed of silicon, a hydrogenated amorphous silicon thin film, a sputtered silicon thin film, a silicon germanium thin film and a dehydrogenated amorphous silicon thin film.

The angle of incidence of said monitor light on said thin film is the same as an angle at which a reflection intensity of P polarization of said thin film in at least one of before and after said annealing processing becomes the minimum, and wherein an incident light beam of said monitor light on said thin film is either S polarization or the P polarization. By measuring the reflected light of the P polarization at an angle where the reflection intensity of the P polarization becomes the minimum, an effective measurement can be realized in comparison with when using a random polarization.

Further, the intensity distribution of the monitor light may be equalized. For example, a proper lens optical device such as a homogenizer can be used. Also, the monitor light may be a laser beam.

DETAILED DESCRIPTION OF THE PREFERRED EMBODIMENTS

Figure 1:
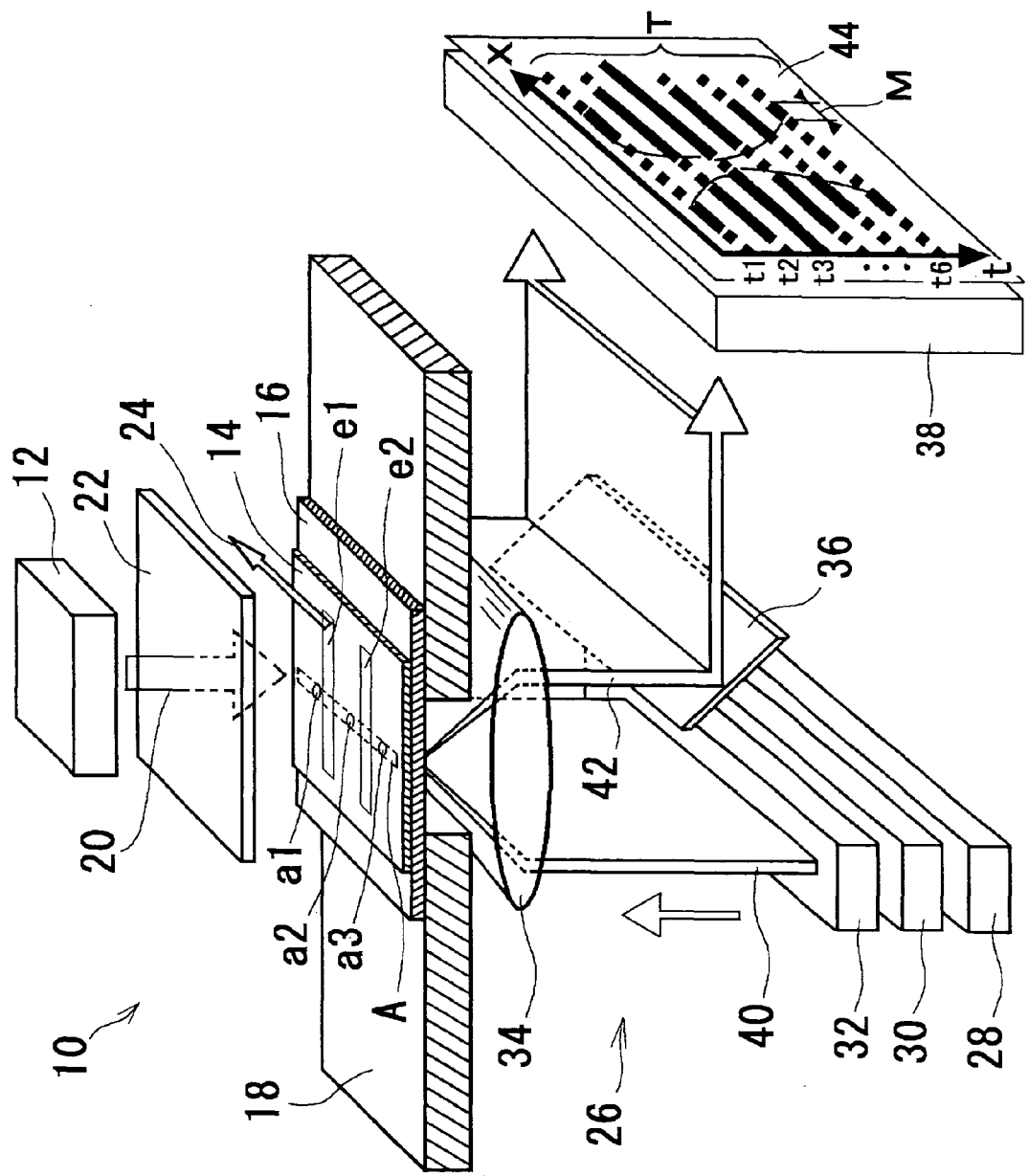
FIG. 1 is a perspective view showing an embodiment of the apparatus for in-situ monitoring of crystallization state according to the present invention.

Referring to FIG. 1, an annealing apparatus 10 using a pulsed laser beam as an energy line is provided with an annealing laser equipment 12, and an XY stage drive mechanism not shown for two-dimensionally moving a sample table 18 which attaches removably a substrate 16 having a thin film 14 to be annealed (hereinafter to be called "annealed thin film 14"). The illustration shows only a part of the sample table 18.

As a source of an annealing laser beam to be used in the annealing laser equipment 12, it is possible to use, for example, a ruby laser, yttorium aluminium garnet (hereinafter called "YAG") laser, excimer laser and the like.

The annealing laser equipment 12 is a pulsed laser light source equipment, which outputs a predetermined energy light necessary for melting an irradiated thin film. The annealing laser equipment 12 usually generates a laser beam having energy of about 1 J per pulse at a pulse time of 20–100 nano seconds (hereinafter called "ns"). In the illustration, krypton fluorine (hereinafter called "KrF") laser is used as the annealing laser equipment and generates a laser beam having a pulse width of about 25 ns at the rate of 100 times per second.

An irradiation area of 5 mm. can be selected as the irradiation area of the annealing laser beam 20 to irradiate a thin film to be annealed so that the annealing laser equipment 12 can irradiate, for example, a plurality of the thin films to be annealed arranged in a plane.

Though not shown, the annealing laser equipment 12 includes a resonator for laser oscillation, and a lens system for reshaping the laser beam into a beam shape suitable for irradiation.

As the thin film 14 to be annealed, it is possible to use a film-formed amorphous semiconductor thin film such as, for example, a thin film whose main component is silicon, a hydrogenated amorphous silicon thin film, a sputtered silicon thin film, a silicon germanium thin film and a dehydrogenated amorphous silicon thin film, etc. In the illustration, a film-formed amorphous silicon thin film is used. As the amorphous silicon, the dehydrogenated amorphous silicon can be generally used. While these thin films have a light reflecting property or a light transmitting property to be varied by the conductivity of the films depending on the film quality, the intensity of reflected light or transmitted light of the film are almost same when the thin films are melting.

As the substrate 16, it is possible to use a transparent glass substrate, a transparent plastic substrate, a silicon substrate or the like. In the illustration, a transparent glass substrate is used.

The glass substrate 16 having the amorphous silicon thin film 14 is attached removably to the sample table 18 and located at a predetermined position. The illustration shows the amorphous silicon thin film 14 and the glass substrate 16 only partially.

The annealing apparatus 10, in the illustration, further has a phase shifter support not shown which supports a phase shifter 22 so that the phase shifter 22 can be used. The phase shifter 22 has a shifter portion for selectively shifting the phase of a light via the phase shifter. The phase shifter 22 having the shifter portion does not cause any loss of light (e.g., loss of light quantity) in filtering action on the incident laser beam, minimizes the intensity of the light incident on the shifter portion and passes the light as a light having a light intensity distribution of an inverted peak pattern. The amorphous silicon thin film 14 is irradiated by the annealing laser beam 20 the via the phase shifter 22 so that an intensity distribution of irradiation can be formed. The phase shifter will be described later.

According to the intensity distribution of irradiation on the amorphous silicon thin film 14, a difference is caused in energy distribution of the laser beam 20 into the thin film, so that the crystallization of the thin film or acceleration of the crystallization is efficiently carried out. In the illustration, regions e1 and e2 having a great irradiation intensity by the laser beam 20 via the phase shifter 22 are generated. Crystal grains generated within the regions e1 and e2 grow, for example, in the direction of e2 to e1 of the amorphous silicon thin film 14, namely, the direction of the arrow 24 parallel to the surface of the substrate.

The apparatus 26 for in-situ monitoring of crystallization state comprises a light source equipment 28 for monitoring, a reshaping optical device 30, a homogenizer 32, an object lens 34 for image formation, a reflecting mirror 36, and a measuring device 38. "In-situ monitoring" means, as described later, observing information related to a film quality during the process from melting to solidifying and crystallizing of the thin film.

As a monitoring laser beam source to be used for the light source equipment 28 for monitoring, it is possible to use, for example, Ar laser, helium neon (hereinafter called "He—Ne") laser, YAG laser and the like. The light sources thereof can generate a laser beam in the range of a wavelength sensitive zone of a photoelectric surface in photoelectric conversion.

The light source equipment 28 for monitoring is a continuous wave laser (hereinafter called "CW laser") light source equipment and generates a laser beam having, for example, a power of 10 mW and a beam diameter of about 5 mm. The beam diameter of a laser beam irradiating the substrate from the light source equipment 28 for monitoring is desirably equal to the beam diameter of the annealing laser beam 20 or smaller than it. In the illustration, the YAG laser generating a light which has a wavelength of about 532 nm is used as a laser equipment for monitoring.

The light source equipment 28 for monitoring is connected to a timing device not shown which is connected to the annealing laser equipment 12. The timing device, in which the starting time for generating the monitor light selectively determined in advance on the basis of the starting time for generating the annealing laser beam is set, sends a signal to start producing the monitor light to the light source equipment 28 for monitoring. In the illustrated example, a signal to start generating the monitor light simultaneously with the start of generation of the annealing laser beam is sent from the timing device to the light source equipment 28 for monitoring.

The reshaping optical device 30 is an optical device for reshaping the sectional shape of the laser beam started from the light source equipment 28 for monitoring into a predetermined shape, and acts as a monitor light reshaping instrument. In the illustration, the reshaping optical device 30 reshapes the laser beam started from the light source equipment 28 for monitoring into a laser beam having a rectangular sectional shape which has short sides relative to the section of the laser beam and long sides which are extremely long in comparison with the short sides.

The homogenizer 32 converts the laser beam via the reshaping optical device 30 into a laser beam having a uniform light intensity distribution in the section of the laser beam. For example, the light intensity distribution in the section of the YAG laser beam is a light intensity distribution based on the Gaussian distribution and is not a uniform intensity distribution. The YAG laser beam, by passing the homogenizer 32, is converted into a laser beam having a uniform light intensity distribution in the section of the laser beam.

The object lens 34 for image formation forms images of a plate-like laser beam 40 having a rectangular sectional shape of a uniform light intensity distribution via the reshaping light source equipment 30 and the homogenizer 32 as a monitor light having a rectangular sectional shape having a specific ratio of the short side and the long side relative to the sectional shape of the laser beam on the amorphous silicon thin film 14.

In the illustration, the underside of the amorphous silicon thin film 14, the underside facing the glass substrate 16, is irradiated by the laser beam 40 for monitoring through the glass substrate 16, and the laser beam 40 for monitoring is imaged on the underside of the amorphous silicon thin film 14 as a monitor light having a strip-like section of 60 .m×1 .m in dimension.

The underside of the amorphous silicon thin film 14 is irradiated by the laser beam 40 for monitoring, and the laser beam 40 for monitoring is imaged on the underside of the amorphous silicon thin film 14 such that the longitudinal direction of the strip-like section of the laser beam becomes orthogonal to the longitudinal direction of the regions e1, e2 where the irradiation intensity of the annealing laser beam caused by the phase shifter 22 is great. An irradiation area A of the laser beam 40 for monitoring is formed on the underside of the amorphous silicon thin film 14.

The irradiation area A of the laser beam 40 for monitoring is formed as a region including a plurality of monitoring places as well as monitoring places a1, a2 and a3 in predetermined positions.

At least a part of the laser beam 40 for monitoring which has been applied to irradiate the amorphous silicon thin film 14 starts as a reflected light 42 again from the underside of the amorphous silicon thin film 14. The intensity of the reflected light 42 of the laser beam 40 for monitoring depends on the angle of incidence on the amorphous silicon thin film 14, a Fresnel coefficient calculated by the refractive index or extinction coefficient of the amorphous silicon thin film 14, and an interference phenomenon within the amorphous silicon thin film 14.

The object lens 34 further receives the reflected light 42 from the amorphous silicon thin film 14 due to the irradiation onto the region A of the underside of the amorphous silicon thin film 14 with the laser beam 40 for monitoring. The reflecting mirror 36 is a movable mirror capable of changing the orientation of the reflecting surface, receives the reflected light 42 via the object lens 34 on the reflecting surface and changes the advancing direction of the reflected light 42.

The measuring device 38 receives the reflected light 42 via the reflecting mirror 36, makes the received light incident on the photoelectric surface and by generating the photoelectron to subject the light to photoelectric conversion, passes the photoelectron through a field which varies with time, and makes the passed electron reach a display screen such as, for example, a phosphor substance, to display it as a monitor signal. That is to say, a projected image P corresponding to the electron intensity, that is, the number of electrons of the photoelectron is formed in the display screen (in the illustration, phosphor), and the temporal change of the intensity distribution of the projection image P is measured and displayed in a display portion 44. The rate of the temporal change of the field is determined according to the speed of the change from melting to solidifying of the thin film. For example, if the thin film changes from melting to solidification and crystallization within 10 ns, it is sufficient to determine the rate so that the temporal change of the intensity distribution of the projection image P corresponding to the change of the film quality within 10 ns can be measured.

The temporal change of the intensity of the reflected light from each of all the places including the places a1, a2 and a3 for monitoring within the region A irradiated by the monitoring laser beam 40 can be observed or measured as the light intensity distribution of the reflected light 42 related to each of the places.

In the illustration, the relation between the measuring time t and a longitudinal position X within a strip-like section of a place for monitoring in a total measuring time T of the reflected light 42 is graphed relative to the intensity of the projected image P. To facilitate understanding, FIG. 1 shows an example of displaying the respective intensities of the reflected light 42 at time t1, t2, t3, . . . t6 every 10 ns when the total measuring time T is set as 60 ns. The total measuring time T and the time t1, t2, . . . are not limited to this example.

Also, in the foregoing graph, in order to facilitate understanding, a case where the annealed thin film is melted and the intensity of the reflected light is great is shown by a solid line, while a case where it is solidified and the reflection intensity is small is shown by a dotted line. That is to say, the solid line portion shows that the annealed thin film is melted to be in a state of the liquid phase, and the length M of the solid line portion shows a melting width of the annealed thin film at each the time t1, t2, t3, . . . t6. The temporal change of the melting width M is displayed in the display portion 44.

The temporal change of the melting width M is displayed in the display portion 44 and simultaneously observed two-dimensionally in a plane. In other words the temporal change relative to melting at every monitoring place within the irradiated region A is observed two-dimensionally at the same time in a plane.

Figure 2:
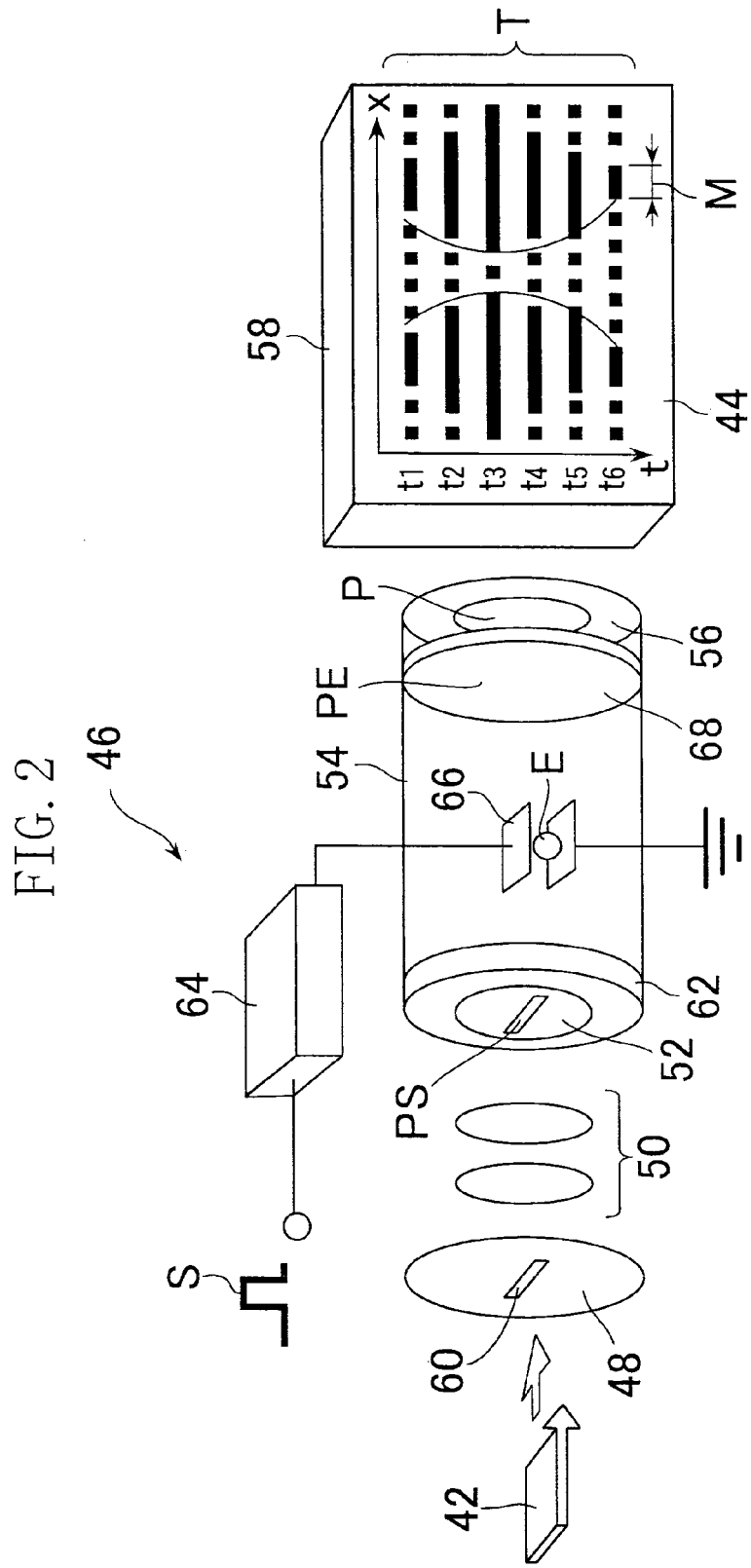
FIG. 2 is a perspective view showing an embodiment of a measuring device to be used in the apparatus for in-situ monitoring of crystallization state as shown in FIG. 1.

As a measuring device 38, a device using a streak camera which converts an optical image into a photoelectron beam image and reconverts it into the optical image can be used. With reference to FIG. 2, the streak camera 46 has a slit plate 48, a group of lenses 50, a photoelectric converter 52, a field generator 54, a phosphor screen, and an image measuring device 58.

The slit plate 48 has a slit 60 for receiving the reflected light 42 and regulating the passage of the reflected light 42 to be shaped like a strip. The lens group 50 receives the light passing through the slit 60 and forms an image of the received light as a slit image PS in the photoelectric converter 52.

The photoelectric converter 52 receives the light passing through the lens group 50 and releases the photoelectron corresponding to the received light to generate a photoelectric conversion signal.

The streak camera has, for example, the field generator 54 so as to take out a photoelectron as a signal changing with time. The field generator 54 passes the photoelectron generated in the photoelectric converter 52 through the field changing with time. The field generator 54 which is a electrostatic accelerator and deflector comprises: an accelerating electrode 62 for promptly and efficiently imaging a converted photoelectron on the phosphor screen; a sweep electrode 66 for changing an advancing direction of an electron E from the accelerating electrode 62 according to a trigger signal S by a sweep circuit 64; and an electron multiplier 68 for multiplying the electron passing through the sweep electrode 66.

In the electron multiplier 68, a image PE of the electron is essentially formed, and the phosphor screen 56 receives the electron passing through the electron multiplier 68 and forms the projection image P corresponding to the electron.

The image measuring device 58 extracts data of the intensity distribution of the projection image P at each time t1, t2, t3, . . . , processes the data of the analogically measured intensity distribution of the projection image P at each time and displays the same in time series in the display portion 44.

The streak camera 46 has the laser beam 40 for monitoring converted into a photoelectron and has the photoelectron scanned in the direction orthogonal to the longitudinal direction of the strip-like section of the laser beam 40. The projection image P projected on the phosphor screen 56 can be dealt with as secondary information, so that, for example, when the projection image is picked up with a CCD camera and converted into digital information, it is possible to store the digital information in a digital memory or process it by a computer. The digital information can be displayed properly.

In the embodiment, furthermore, to determine the time to start measuring the reflected light 42 by the streak camera 46, there are disposed a photo detector not shown and a display unit not shown. The photo detector detects the laser beam by a high-speed photo diode through an attenuation filter not shown disposed in a part of the route of the annealing laser beam. A delaying device outputs the trigger signal for starting the measurement of the reflected light 42 by the streak camera 46 after a lapse of a delay time which is selectively determined in advance on the basis of a detection time.

An explanation follows with reference to FIG. 1 on the method of in-situ monitoring of the crystallization state using the apparatus for in-situ monitoring of the crystallization state.

Firstly, a transparent glass substrate 16 having the amorphous silicon thin film 14 is attached to a predetermined position of the sample table 18, and the sample table 18 is moved to the predetermined position stage drive mechanism.

Next, A KrF laser beam set at a predetermined power density by the annealing laser equipment 12 is generated at a pulse width of about 25 ns at the rate of 100 times/second, and the laser beam is irradiated only for 25 ns on the surface of the amorphous silicon thin film 14 via the phase shifter 22.

Simultaneously with the start of generation of the annealing KrF laser beam, a signal to start generating the monitoring YAG laser beam is sent from the timing device to the monitoring light source equipment 28, which irradiates a YAG laser beam of about 532 nm at a predetermined power density.

The irradiated YAG laser beam is imaged on the underside of the amorphous silicon thin film 14 as the laser beam 40 for monitoring having a strip-like section of 60 .m×1 .m in dimension via the reshaping optical unit 30, the homogenizer 32 and the object lens 34 and through the glass substrate 16.

The reflected light 42 from the amorphous silicon thin film 14 is incident on the measuring device 38 via the object lens 34 and the reflecting mirror 36, and the temporal change of the intensity distribution of the projection image corresponding to the intensity distribution including the intensity distribution of the reflected light 42 is displayed in the display portion 44. That is to say, the crystallization state is measured and displayed as a light intensity distribution related to the position of a monitoring place.

In the apparatus and method of in-situ monitoring of crystallization state, it is possible to set the incidence angle of the monitor light on the annealed thin film at an angle at which the reflection intensity of the P polarization at the annealed thin film either before or after the annealing becomes the minimum, that is, the angle of polarization. In this case, the angle of polarization is determined by the optical constant and the film thickness of the annealed thin film, the optical constant and film thickness of a grounding substrate as well as interference inside the annealed thin film. Also, the light incident on the annealed thin film of the monitor light may be either the S polarization or the P polarization. The minimum value of the reflection intensity of the P polarization is smaller than the minimum value of the reflection intensity of the S polarization, and the maximum value of the reflection intensity of the P polarization and the maximum value of the reflection intensity of the s polarization are approximately equal. Since by measuring the reflection intensity of the P polarization a great change is obtained between the minimum value and the maximum value in the reflection intensity, it is favorable with respect to improvement in the S/N rate in measurement.

The method and apparatus for in-situ monitoring of crystallization state described above can be changed as follows.

While the annealing method and apparatus use a phase shifter when annealing, a method and an apparatus for annealing without using a phase shifter at the time of annealing will do.

In the method and apparatus for in-situ monitoring of crystallization state, instead of irradiating by the monitor light a underside of the annealed thin film, which is different from the side to be, irradiated by the annealing energy line to, that is, the underside of the annealed thin film, the monitor light may be irradiated on the same side as the side to be irradiated by the annealing energy line, that is, the surface of the annealed thin film, or both surface and underside may be irradiated by the monitor light.

Figure 3:
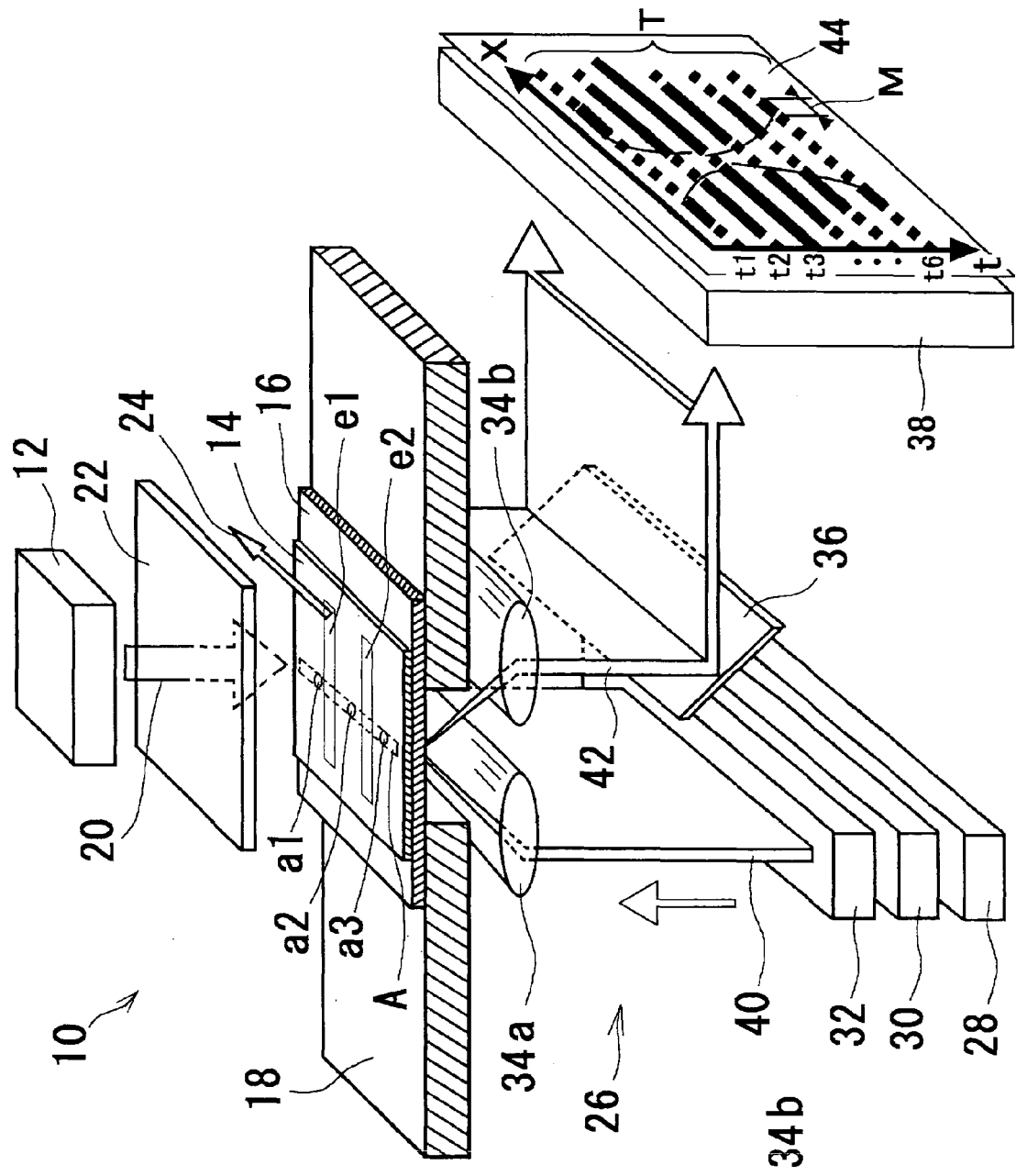
FIG. 3 is a perspective view showing another embodiment of the apparatus for in-situ monitoring of crystallization state according to the present invention.

In the method and apparatus for in-situ monitoring of crystallization state, instead of making the object lens to receive the monitor light from a monitor light source equipment and the object lens to receive the reflected light of the monitor light from the annealed thin film the identical lens, it is possible, as shown in FIG. 3, to make the object lens to receive the monitor light from the monitoring light source equipment and the object lens to receive the reflected light from the annealed thin film of the monitor light different lenses (e.g., two lenses 34a and 34b). The annealing apparatus 10 shown in FIG. 3 is the same as the annealing apparatus 10 shown in FIG. 1. The same portion as in FIG. 1 is put the same reference numeral, and detailed explanation thereof is omitted for avoiding redundancy. The same portions of an apparatus 70 for in-situ monitoring of crystallized state are put the same reference numerals as in the apparatus 26 for in-situ monitoring of crystallization state shown in FIG. 1, and detailed explanation there is omitted for avoiding redundancy.

In the method and apparatus for in-situ monitoring of crystallization state, instead of monitoring the crystallization state of the annealed thin film by using the reflected light from the annealed thin film of the monitor light, it is possible to monitor the crystallization state of the annealed thin film by using the transmitted light from the annealed thin film of the monitor light, or it is possible to monitor the crystallization state of the annealed thin film by using a light having a smaller intensity than the reflected light from the annealed thin film of the monitor light, that is outgoing from the thin film, scattered within the annealed thin film.

In the method and apparatus for in-situ monitoring of crystallization state, in case the reflected light of the monitor light from the annealed thin film has a relatively great intensity, an attenuating filter may be disposed ahead of the streak camera.

In the method and apparatus for in-situ monitoring of crystallization state, in addition to the strip-like monitor light as mentioned above, it is possible to measure a crystal growth, i.e., a melting region in another direction by irradiating the annealed thin film by a second monitor light having a different wavelength in the direction orthogonal to the longitudinal direction of the strip-like section of the monitor light and using the streak camera via a photoelectric converter.

Figure 4:
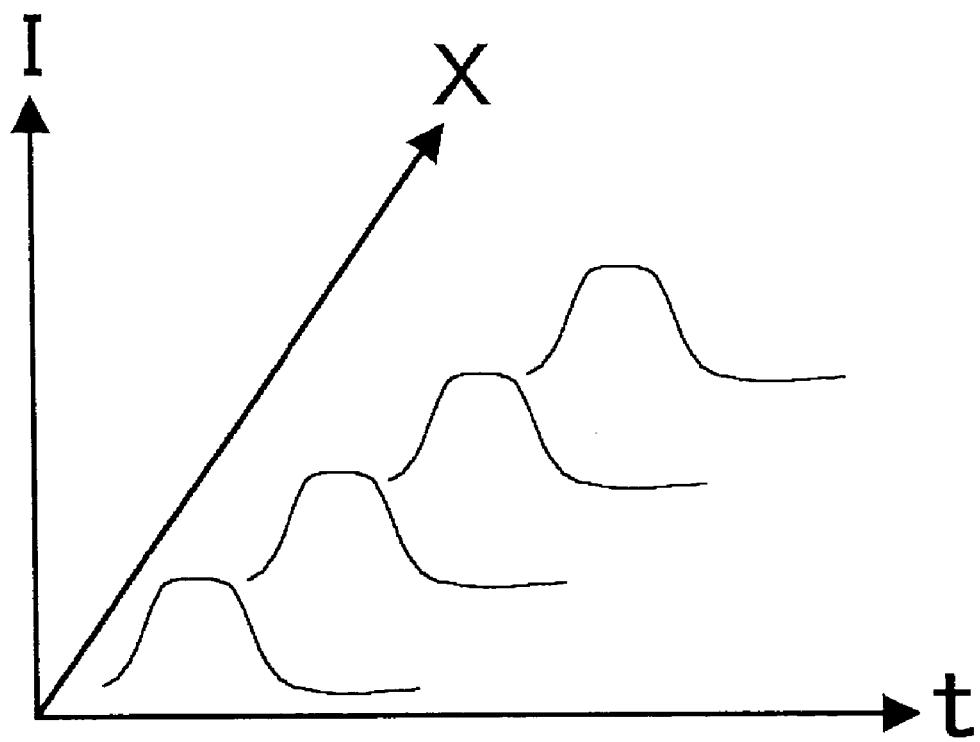
FIG. 4 is a graph showing a relationship among a measurement time t, a position X and a light intensity I for another embodiment of the method of in-situ monitoring of crystallization state according to the present invention.

For example, as shown in FIG. 4, in addition to measuring the relationship between a measurement time $t$ of the reflected light or the transmitted light from the annealed thin film by the first monitor light and a longitudinal position X within the strip-like section of a monitoring place, by measuring a progress of change in real time between the measurement time $t$ of the reflected light or the transmitted light from the annealed thin film by the second monitor light and the reflected light intensity I at each monitoring place, it is possible to obtain as three-dimensional information a light intensity distribution including the temporal change of the reflected light or the transmitted light from the annealed thin film by the monitor light. The temporal change of this light intensity is a feature showing a change from melting to solidification of the thin film by laser irradiation during the pulse width of 25 nsec. Also, this feature is measured during the melting period of the thin film (generally, several decade nano seconds—several hundred nano seconds). That is to say, it is possible to measure as a light intensity related to the position of a monitoring place. Further, the result of this measurement may be displayed.

While, in the embodiment shown in FIG. 1, the monitoring laser beam is reshaped into a light having a strip-like section of 60 .m×1 .m, the shape of the section of the monitoring laser light is not limited to this in section area and section shape. For example, in case of using a light source equipment irradiating by a monitor light having sufficient power or the power of the monitor light started from the light source equipment can be ensured, it is possible to reshape the monitor light to a monitor light having a circular or elliptical section with a large area instead of a strip-shaped or a rectangular section, to irradiate the annealed thin film with the reshaped monitor light and converge and image the reflected light or the transmitted light from the thin film ahead of the photoelectric converter to reshape.

An annealing method and apparatus for forming a crystal grain (single crystal grain) as well as the method and apparatus for in-situ monitoring of crystallization in annealing are explained with reference to FIG. 5.

Figure 5:
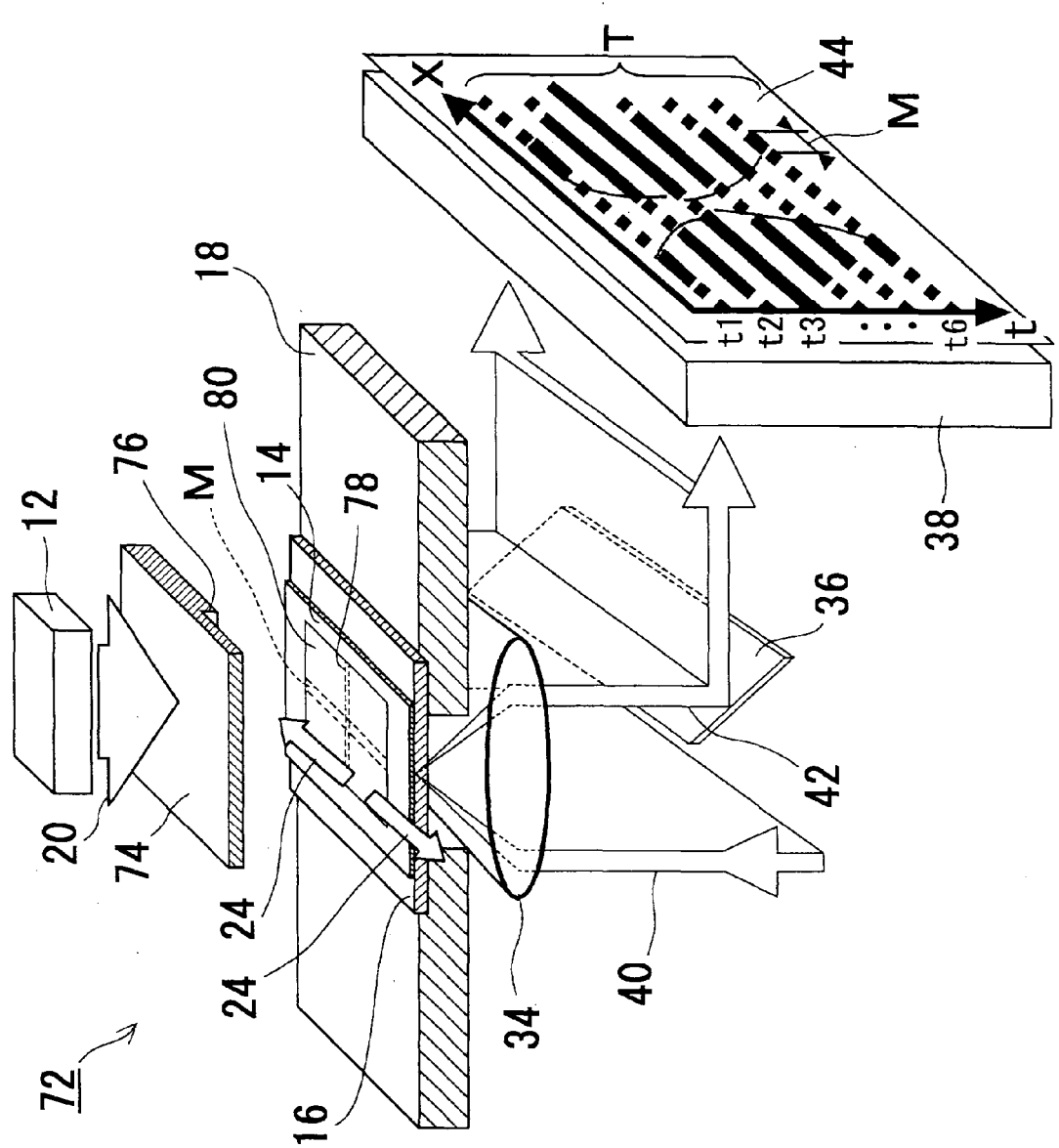
FIG. 5 is a perspective view showing yet another embodiment of the apparatus for in-situ monitoring of crystallization state according to the present invention.

In FIG. 5, an annealing apparatus 72 has a similar structure to the annealing apparatus 10 in FIG. 1. The parts identical with those in FIG. 1 are put the same reference numerals, and detailed explanation thereof will be omitted because of redundancy.

The annealing apparatus 72 in the illustration further has a phase shifter support not shown for supporting a phase shifter 74 so that the phase shifter 74 can be used. The phase shifter 74 has a shifter portion, that is, a staged portion 76 in the illustration, for selectively shifting a phase of a light passing the phase shifter 74. The annealing laser beam 20 irradiates the amorphous silicon thin film 14 through the phase shifter 74 so that an intensity distribution of irradiation can be formed.

Figure 6:
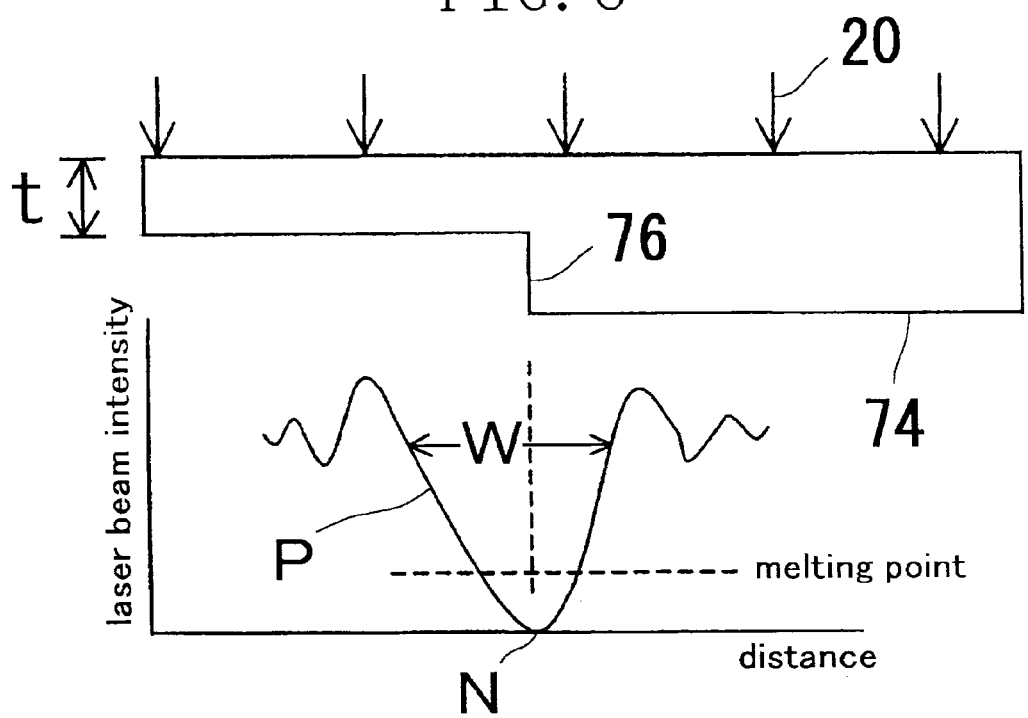
FIG. 6 is a graph showing a change in the laser beam intensity by a phase shifter.

Here is an explanation of the above-mentioned phase shifter. The phase shifter is intended to form a difference in stage of a thickness in a transparent medium, e.g., a quartz base material, and at the border of the difference, an incident laser beam is made to interfere with the diffraction light to give a periodic spatial distribution to the intensity of the incident laser light. FIG. 6 shows a change in the laser beam intensity due to the phase shifter. In the embodiment shown in FIG. 6, concerning the laser beam 20, a case where the position of the staged portion 76 forming the shift portion of the phase shifter 74 is X=0 and with the position as a boundary a phase difference of 180 is given. That is to say, the laser beam which passed a thick part of the phase shifter 74 is delayed in comparison with the laser beam passing the thin part ($t$ in thickness). As a result of mutual intervention and refraction between these laser beams, a passing laser beam intensity distribution as shown in FIG. 6 is obtained. In general, supposing the wavelength of the laser beam is the film thickness $t$ of a transparent medium for giving a phase difference of 180° to a transparent medium with a refractive index $n$ can be expressed by the following equation.

[Formula 1]

$$t=/2(n-1) \qquad \text{Expression (1)}$$

For example, in case the wavelength of the KrF excimer laser beam is 248 nm and the refractive index of the quartz base material is 1.508 at the wavelength of 248 nm, the difference in stage for making a phase difference of 180° is 244 nm, and it suffices to make a stage difference of 244 nm at a predetermined position in the quartz base material. A stage difference in the quartz base material can be given, for example, by selectively etching by a gaseous phase or a liquid phase. For giving a stage difference, it is possible to selectively form a light transmitting film, e.g., $SiO_2$, by plasma CVD, decompression CVD, etc.

A part of the laser beam incident on the phase shifter 74 is interfered by the phase difference at the stage difference portion 76, so that the amount of its light transmittance becomes the minimum N, and transmits as a light having such a light intensity distribution as a light whose intensity falls rapidly. The light intensity distribution showing such a minimum transmitting light is called an inverse peak pattern P. A characteristic of the inverse peak pattern is not to show filter-like attenuation of the incident ray 20. This characteristic results in a great single crystallization. A laser beam having a light intensity distribution of such an inverse peak pattern P incident on an amorphous silicon layer raises the temperature of a part of the amorphous silicon layer, and a part of a low temperature silicon around it becomes a core of a crystal, thereby causing a crystal growth in a direction normal to the stage difference which forms the phase difference, namely, in the lateral direction, which forms a large crystal grain. The inverse peak pattern P is approximately wedge-shaped (e.g., U- or V-shaped).

Figure 8:
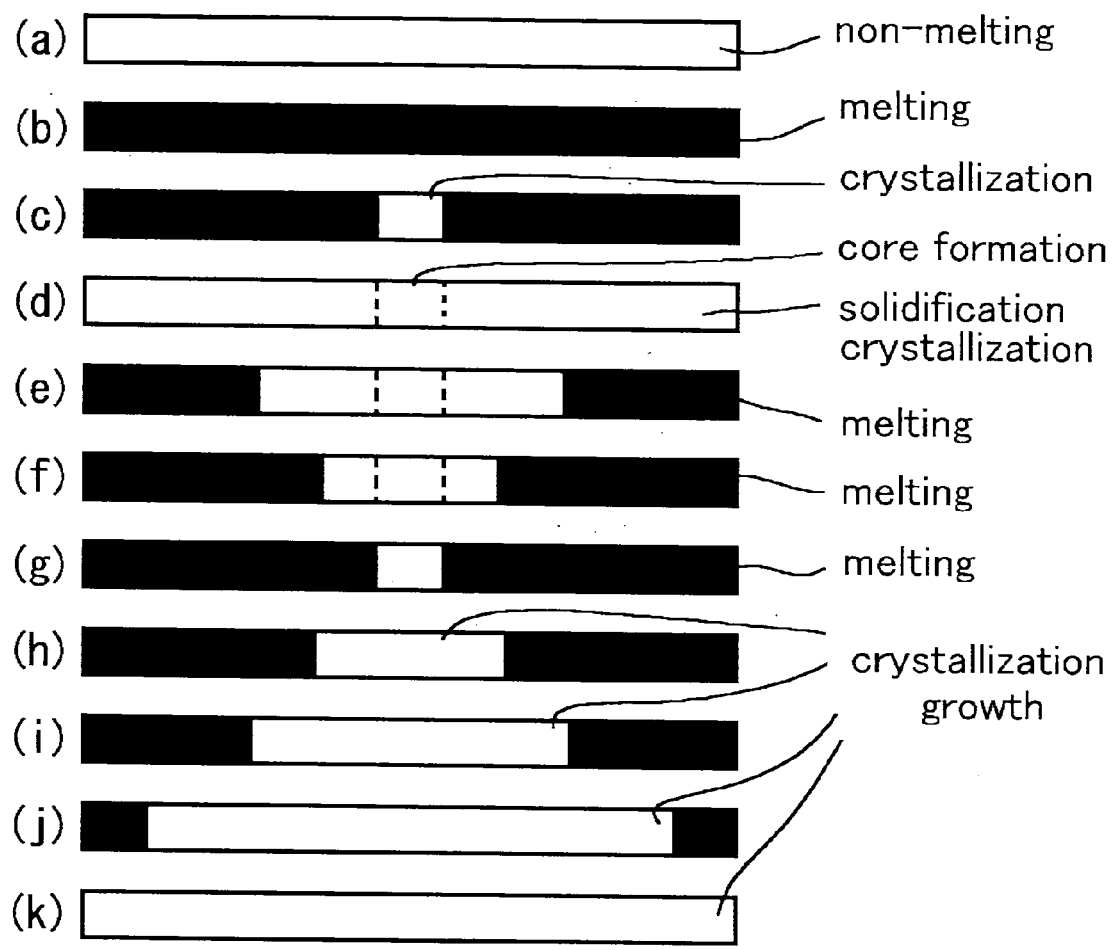
FIG. 8 is a graph showing yet another embodiment of the method of in-situ monitoring of crystallization state according to the present invention and showing an observation result at a real time of a process from before melting of the thin film, core formation, solidification until crystallization.

The amorphous silicon thin film 14 is in a non-melted state before the irradiation by the annealing laser beam. When the crystallization state is monitored by irradiating with the monitor light, the display portion 44 of the measuring device 38 displays as shown in FIG. 8(a).

The KrF laser beam set at a predetermined power density is generated from the annealing laser equipment 12 at a predetermined pulse width, the surface of the amorphous silicon thin film 14 is irradiated by the laser beam through the phase shifter 74, to irradiate the leaser beam. By this, melting of the amorphous silicone thin film 14 starts in the laser beam irradiation region at the melting point or higher. When all the parts of the laser beam intensity of the inverse peak pattern in FIG. 7 take a value of the melting point or over, it generally gets into a molten state. This molten state is displayed by the monitor light in the display portion 44 of the measuring device 38 as shown in FIG. 8(b).

Figure 7:
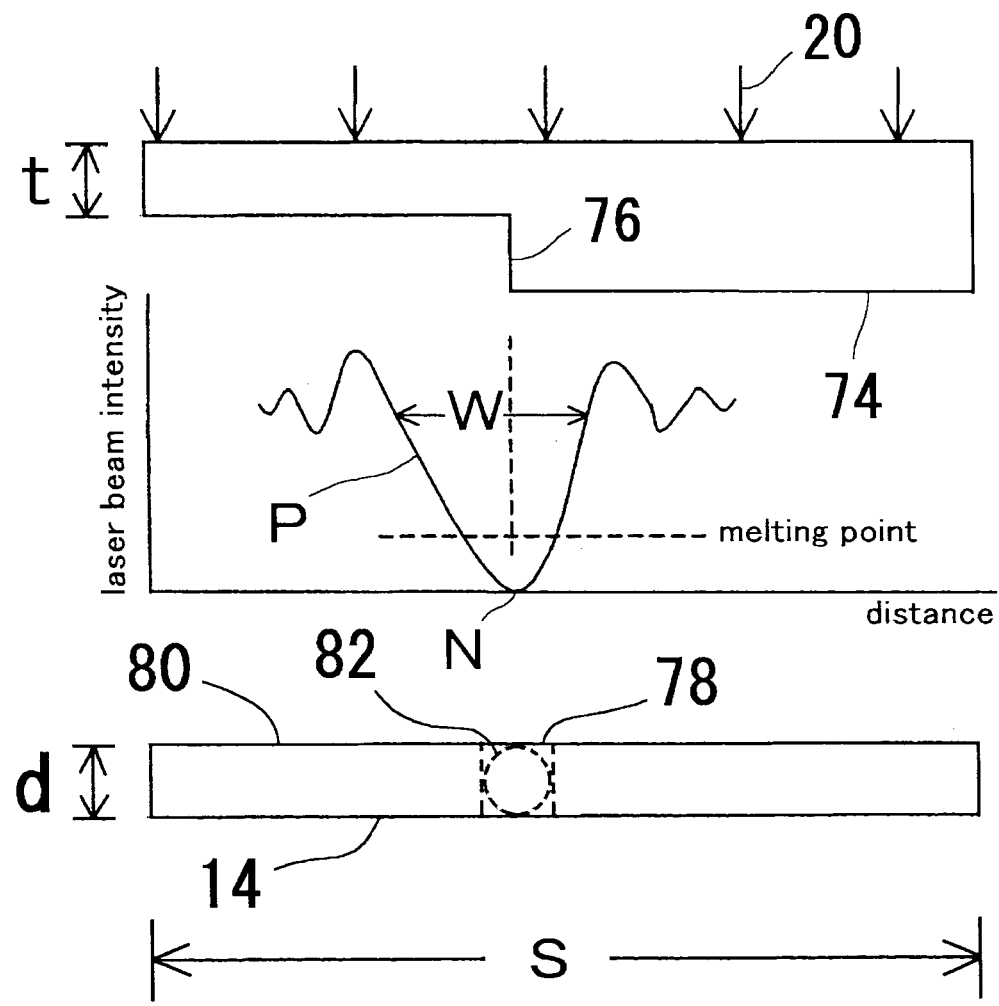
FIG. 7 is a graph showing the change of the laser beam intensity and the formation of a core of the crystal growth.

The formation process of the crystal core will be explained with reference to FIG. 7. The intensity of the laser beam which passed the stage difference portion 76 or very near it is smaller than the intensity of the laser beam 20 which passed the other part of the phase shifter 74. Consequently, the light intensity distribution at a region S of the amorphous silicon thin film 14 subjected to the irradiation by the laser beam 20 which passed the stage difference portion 76 and very near it is as follows. The temperature of the region 78 at the irradiation area at the minimum N of the inverse peak pattern is lower than the temperature of the other region 80 of the amorphous silicon thin film 14, and the same as or lower than the temperature of the melting point of the thin film 14 at the minimum value. The temperature of the other area 80 is the same as or higher than the melting point of the thin film 14. For this reason, solidification of the silicon within the region 78 starts earlier than solidification of the silicon within the other region 80 (FIG. 8(c)), and then, the silicon within the other region 80 solidifies, a core 82 which becomes a start point of the lateral crystal growth is formed, and the crystal growth is started in the lateral direction (FIG. 8(d)). Here, as shown in FIG. 7, the core 82 has been formed within the region 78 of the amorphous silicon thin film 14. The same reference numerals are given to the identical portions as in FIG. 6 and a detailed explanation on them are omitted.

Next, the crystallization process is explained in more detail. The KrF laser beam set at a predetermined power density is generated by the annealing laser light source equipment 12 at a pulse width of about 24 ns at the rate of 100 times per second, and the amorphous silicon thin film 14 is irradiated by the laser beam through the phase shifter 74 for only 25 ns. A condition of this laser beam intensity pattern is selected to such a degree as the time for melting the silicon core 82 within the area 78 of the amorphous silicon thin film 14 is the shortest or as the core 82 is not melted.

The intensity of the laser beam which passed the stage difference portion 76 and very near it is a minimum light intensity smaller than that of the laser beam which passed the other portion of the phase shifter 74. The temperature of the region 78 of the amorphous silicon thin film 14 irradiated by the laser beam which passed the stage difference portion 76 and very near it is lower than the temperature of the other region 80 of the amorphous silicon thin film 14 so that the core 82 of the silicon within the region 78 may not be melted or that the melting time of the core 82 may be the shortest. Consequently, melting of the silicon within the other region 80 of the amorphous silicon thin film 14 begins, and the molten region spreads by thermal conduction toward the vicinity of the region 78 where the core 82 is formed. On the other hand, the region 78 and its vicinity where the core 82 is formed remain to be in a non-molten state or a molten state only for a short time. In the display portion 44 of the measuring device 38, as in FIGS. 8(e)–(g), an aspect in which the molten region spreads with the time can be displayed.

Thereafter, the spread of the molten region reaches the vicinity of the region 78, and a change from melting to solidification, i.e., crystallization is caused. With the core 82 as an origin, solidification and crystallization of the molten silicon begins outward of the core successively. That is to say, with the core 82 as a base, the lateral crystal growth progresses to form a large crystal grain. In the display portion 44 of the measuring device, it is displayed as in FIGS. 8(h)–(k).

On the basis of a result of real-time observation in the process of before melting, after melting, solidification and crystallization of the thin film, a reasonable condition of the irradiation by the energy line for the lateral crystal growth of the thin film can be obtained. It is, therefore, possible to form a large crystal grain. In this way, the variation from solid phase to melting—crystallization when amorphous Si having a film thickness of about 50 nm–300 nm is irradiated by a pulsed light for several-hundred nano seconds is a substantially instantaneous phenomenon for several-hundred nano seconds. This is a phenomenon for several decade nano seconds, and this phenomenon is measured. By this measurement, a light intensity distribution for the optimum crystallization is calculated, and a uniform crystallization process over a broad area can be realized. The uniform crystallization process is the most suitable for a display unit such as a liquid crystal display unit with a large screen. That is to say, it realizes a display without non-uniformity, flaw, spot and the like and a high-quality screen, particularly adapted to digitalization. Further, because instantaneous measurement is possible, the greater the spread width of the inverse peak pattern P shown in FIGS. 6 and 7 is, the larger crystallization is enabled, and the optimum spread width W can be obtained. Moreover, because instantaneous measurement is possible, previous irradiation of the inverse peak pattern enables to display a successively changing solid-liquid boundary face. For example, in the production of a thin film transistor, an active layer or a channel region can be made of one crystal particle. In other words, the channel region can be formed substantially by a single crystal.

The present invention is not limited to the above embodiments but can be variously modified without departing from its spirit.

What is claimed is:

1. A method of in-situ monitoring of a crystallization state in annealing processing through irradiation of a thin film by an energy line having a light intensity distribution of an inverted peak pattern for at least one of crystallization of said thin film and promotion of the crystallization, melting an irradiation region or growing said crystallization laterally after termination of said energy line irradiation, comprising:
   simultaneously irradiating, by a monitor light, at least a plurality of monitoring places in a region having a predetermined area of at least one of the surface and the underside of said thin film directly or through a substrate, at least during or after one of before, during or after said energy line irradiation, said monitor light being for monitoring of the crystallization state of said thin film; and
   measuring a temporal change of the intensity of at least one of a reflected light or a transmitted light, from said surface or said underside of said thin film, said monitor light as a light intensity distribution related to the positions of said monitoring places.

2. A method of in-situ monitoring of a crystallization state according to claim 1, wherein said irradiation by said monitor light in said irradiation step is applied to a slit-like irradiation region of said thin film so that said irradiation by said monitor light is applied simultaneously to said plurality of irradiation positions of said monitor light.

3. A method of in-situ monitoring of a crystallization state according to claim 1, wherein said irradiation by said energy line is an irradiation by a pulsed light.

4. A method of in-situ monitoring of a crystallization state according to claim 1, wherein the reflected light or the transmitted light, from said thin film, said monitor light in said measuring step is detected by a streak camera.

5. A method of in-situ monitoring of a crystallization state according to claim 4, wherein the step of application of said monitor light irradiation step further includes imaging said monitor light on said thin film by means of one object lens and imaging the reflected light from said thin film on a light receiving portion of said photoelectric converter, and make at least one of said reflected light and said transmitted light via said object lens take separate optical paths.

6. A method of in-situ monitoring of a crystallization state according to any one of claim 1, wherein the step of applying said monitor light irradiation comprises reshaping and irradiating said monitor light so that said monitor light may have a section of which the area includes the plurality of irradiation positions of said monitor light on said thin film; and making at least one of the reflected light and the transmitted light from said thin film reshaped to a strip-like shape so as to be incident on a light receiving portion of a photoelectric converter having a photoelectric surface.

7. A method of in-situ monitoring of a crystallization state according to claim 1, wherein said step of applying said monitor light irradiation includes applying an irradiation by a plurality of said monitor lights simultaneously to said plurality of irradiation positions of said monitor light, and making at least one of the reflected light and the transmitted light from said surface or said underside of said thin film incident on the photoelectric converter so that said plurality of lights may align.

8. A method of in-situ monitoring of a crystallization state according to claim 1, wherein said thin film includes at least one of a thin film mainly composed of silicon, a hydrogenated amorphous silicon thin film, a sputtered silicon thin film, a silicon germanium thin film and a dehydrogenated amorphous silicon thin film.

9. A method of in-situ monitoring of a crystallization state according to claim 1, wherein the angle of incidence of said monitor light on said thin film is the same as an angle at which a reflection intensity of P polarization of said thin film in at least one of before and after said annealing processing becomes the minimum, and wherein an incident light beam of said monitor light on said thin film is either S polarization or P polarization.

10. A method of in-situ monitoring of a crystallization state according to claim 1, wherein the step of irradiating by said monitor light further includes equalizing the intensity distribution of said monitor light.

11. A method of in-situ monitoring of a crystallization state according to claim 1, wherein said monitor light is a laser beam in a range of a wavelength sensitive zone of a photoelectric surface.

12. An apparatus for in-situ monitoring of a crystallization state to be used for an annealing processing apparatus for irradiating a thin film by applying an energy line having a light intensity distribution of an inverted peak pattern for at least one of crystallization of said thin film and promotion of the crystallization, melting an irradiation region or growing said crystallization laterally after termination of said energy line irradiation, comprising:

a monitor light irradiating device for irradiating a region, including at least a part of said irradiation region, by a monitor light for monitoring the crystallization state of said thin film; and a measuring device for measuring a temporal change of the intensity of at least one of the reflected light of said monitor light from the surface or the underside of said thin film or the transmitted light through said thin film, as a light intensity distribution related to irradiation positions of said monitor light.

13. An apparatus for in-situ monitoring of a crystallization state according to claim 12, including a monitor light reshaping device for reshaping said monitor light into a strip-like shape so that said monitor light may have a section of which the area includes the plurality of irradiation positions of said monitor light on said thin film.

14. An annealing apparatus using the apparatus for in-situ monitoring of a crystallization state according to claim 12.

15. An annealing apparatus using the apparatus for in-situ monitoring of a crystallization state according to claim 13.

* * * * *